United States Patent
Sciammarella et al.

(10) Patent No.: US 10,466,189 B2
(45) Date of Patent: Nov. 5, 2019

(54) UNIFORM CHILLING CALORIMETER SYSTEM

(71) Applicants: Federico M. Sciammarella, Chicago, IL (US); Joseph S. Santner, Munster, IN (US); Matthew J. Gonser, Steward, IL (US); Justin Whiting, Clarksburg, MD (US); Daniel Nikolov, Batavia, IL (US)

(72) Inventors: Federico M. Sciammarella, Chicago, IL (US); Joseph S. Santner, Munster, IN (US); Matthew J. Gonser, Steward, IL (US); Justin Whiting, Clarksburg, MD (US); Daniel Nikolov, Batavia, IL (US)

(73) Assignee: Board of Trustees of Northern Illinois University, DeKalb, IL (US)

( * ) Notice: Subject to any disclaimer, the term of this patent is extended or adjusted under 35 U.S.C. 154(b) by 270 days.

(21) Appl. No.: 15/493,918

(22) Filed: Apr. 21, 2017

(65) Prior Publication Data
US 2018/0306737 A1    Oct. 25, 2018

(51) Int. Cl.
*G01K 17/00* (2006.01)
*G01K 1/00* (2006.01)
*G01N 25/48* (2006.01)

(52) U.S. Cl.
CPC ................. *G01N 25/4826* (2013.01)

(58) Field of Classification Search
USPC ............................................ 374/31, 33, 208
See application file for complete search history.

(56) References Cited

U.S. PATENT DOCUMENTS

| | | | | |
|---|---|---|---|---|
| 4,925,315 A | * | 5/1990 | Bonnard | G01K 17/00 165/287 |
| 5,876,118 A | * | 3/1999 | Vogel | G01N 25/4826 374/11 |
| 7,261,541 B2 | | 8/2007 | Fong | |
| 8,371,746 B2 | * | 2/2013 | Scharer | G01N 25/486 374/10 |
| 2005/0053115 A1 | * | 3/2005 | Nishimura | G01K 17/00 374/12 |
| 2008/0025364 A1 | * | 1/2008 | Nakatani | G01N 25/20 374/12 |

(Continued)

FOREIGN PATENT DOCUMENTS

CN    102759545 A    10/2012
CN    203479431 U    3/2014

OTHER PUBLICATIONS

Valdemar Malin et al.; Controlling Heat Input by Measuring Net Power; publication; Jul. 2006; pp. 44-50; Welding Journal.

(Continued)

*Primary Examiner* — Mirellys Jagan
(74) *Attorney, Agent, or Firm* — Reinhart Boerner Van Deuren P.C.

(57) ABSTRACT

A calorimeter head and an associated system are provided. The calorimeter head provides symmetric circumferential laminar flow parallel to the bottom plane of a substrate plate of the calorimeter head. The calorimeter head defines a cavity which employs multiple tangentially arranged inlets for receipt of a flow of coolant from a control unit of the system.

24 Claims, 7 Drawing Sheets

(56) References Cited

U.S. PATENT DOCUMENTS

| | | | | |
|---|---|---|---|---|
| 2008/0317089 A1* | 12/2008 | Fontana, Jr. | ............ | G01N 5/025 |
| | | | | 374/33 |
| 2009/0092170 A1* | 4/2009 | Brushwyler | ........... | G01K 17/00 |
| | | | | 374/33 |
| 2011/0286493 A1* | 11/2011 | Torniainen | ............. | B41J 2/1404 |
| | | | | 374/33 |
| 2016/0176118 A1 | 6/2016 | Reese et al. | | |

OTHER PUBLICATIONS

Antonio Armillotta et al.; SLM tooling for die casting with conformal cooling channels; publication; 2014; pp. 573-583; Int J Adv Manuf Technol.

Mehmet A. Sen et al.; A continuous flow microfluidic calorimeter: 3-D numerical modeling with aqueous reactants; publication; Mar. 10, 2015; pp. 184-196; Thermochim Acta.

Dongming Hu et al.; Sensing, modeling and control for laser-based additive manufacturing; publication; 2003; pp. 51-60; International Journal of Machine Tools & Manufacture.

Stratonics; Heat Flow Sensors, Additive Manufacturing, Sensors; pages printed from a website; date last visited Jul. 27, 2017; http://stratonics.com/systems/sensors/.

Ta Instruments; Discover the World's Finest line of Differential Scanning Calorimeters; pages printed from a website; date last visited Jul. 27, 2017; http://www.tainstruments.com.

SLM Solutions; Additive Manufacturing—Your Future?; pages printed from a website; date last visited Jul. 27, 2017; https://slm-solutions.com//products/machines/high-temp-substrate-plate.

Additive Manufacturing; Lawrence Livermore National Laboratory; pages printed from a website; date last visited Jul. 27, 2017; https://manufacturing.llnl.gov/additive-manufacturing.

* cited by examiner

UNIFORM CHILLING CALORIMETER SYSTEM

This invention was made in part with Government support under Grant Number 70NANB13H194 awarded by the National Institute of Standards and Technology. The Government has certain rights in this invention.

FIELD OF THE INVENTION

This invention generally relates to measurement devices and more particularly to calorimeters.

BACKGROUND OF THE INVENTION

There are several manufacturing processes where monitoring energy transfer from a source to a workpiece is highly desirable to achieve accurate solidification manufacturing process control and repeatability. Non-limiting examples of such processes include laser welding as well additive manufacturing, which may use a wide variety of energy input sources.

As is known in the art, electron beam, arc, and laser welding involves directing a directed energy heat source at the interface of mating parts to join the same together at said interface. Monitoring energy transfer to the parts is important as it directly impacts manufacturing characteristics and quality. In certain welding operations, cameras may be utilized to monitor weld bead geometry at the weld point.

Additive manufacturing, or AM, is increasingly being used to manufacture parts of relatively complex geometries. One contemporary AM example involves building up parts by consecutively layering a powder and heating each layer with a laser as it is laid. The directed energy melts the powder forming a melt pool which then fuses to the existing part. This solidification manufacturing process is known as a build, and is done iteratively until a three-dimensional part is formed. Materials used may be metals, plastics, ceramics, etc.

Monitoring and controlling the thermal characteristics of the laser and the part during a build is of critical importance as these thermal characteristics have a direct effect on various characteristics of the finished part, e.g. geometrical accuracy, material properties, residual stresses, etc. A common approach to monitoring such thermal characteristics is to monitor the melt pool size and reduce or increase the power input from the laser accordingly. While this approach has provided some positive results, it does not provide an in depth understanding of the thermal characteristics for controlling AM. Further, such melt pool monitoring typically measures only the build surface (as opposed to a solidification manufacturing process volume) with the use of relatively complex measurement componentry such as infrared cameras and/or sensors.

There is a need for a measurement system which not only provides highly accurate, precise measurement of the modeled active volumetric solidification manufacturing process zone thermal characteristics but also offers a real-time low cost turn-key solution. Such a measurement system would have applicability in any application where it is desirable to measure directed energy input, e.g. electron beam, arc, and laser, used in welding, additive manufacturing, etc. The invention provides such a system. These and other advantages of the invention, as well as additional inventive features, will be apparent from the description of the invention provided herein.

BRIEF SUMMARY OF THE INVENTION

The instant invention has applicability in additive manufacturing, as well as any other solidification manufacturing process where it is desirable to monitor directed energy input to a system during manufacturing. As described above, energy input is a key solidification manufacturing process parameter in additive manufacturing and various forms of welding which controls quality (e.g. residual stress, mechanical, and corrosion properties). With particular reference to additive manufacturing, most of the work done on measurement of energy input in additive manufacturing has been carried out in a research environment. As such, one of the factors that has kept the industry from embracing additive manufacturing is the lack of control of the solidification manufacturing process as both the machine and the feed stock are key to the final quality. Direct measurement of net energy input is a quality control tool for both facets of the quality challenge. The ability to have a real time feedback system provides a means to reduce manufacturing variability, while the net energy validates modeling assumptions like energy source power transfer efficiencies.

Without knowing the thermal efficiency, the thermal efficiency coefficient 'k' as seen below in equation (2), there is no metric to assess how much energy has been absorbed by a build in an additive process. The measurement of energy absorption is critical to have so that a deeper understanding and control of the additive manufacturing process can be established through modeling. This invention provides for an accurate calculation of net energy input. Furthermore, not only can efficiencies be calculated for additive processes, but this data can also contribute to a greater understanding of the sensitivity of metallurgical properties for various build parameters. Energy input H can be defined as the amount of energy that is transferred to the base metal by a source of directed energy per unit of build path trace length. It can be expressed as:

$$H = P_{net}/S \text{ (J/cm)} \quad (1)$$

and so net power $P_{net}$ is defined as:

$$P_{net} = kP_{in} \quad (2)$$

Where $P_{in}$ is the input power generated by the directed energy source in Watts (i.e. laser) and $P_{net}$ is the net power transferred to the substrate in Watts. Another important parameter that often is estimated is the thermal efficiency 'k' which defines the percentage of $P_{in}$ transferred to the substrate. Finally 'S' is the travel speed of the energy source.

With this definition the importance of measuring $P_{net}$ is clear. In addition to its measurement it is also shows how important the thermal efficiency is in determining net power. Therefore, the influence of $P_{net}$ is difficult to overlook. At constant travel speed, $P_{net}$ (rather than $P_{in}$) is directly responsible for all physical and metallurgical changes in the metal being deposited in the metal additive manufacturing process. This includes melt pool shape, single track geometry and integrity (i.e. porosity), metallurgical characteristics (e.g. microstructure and porosity), and mechanical properties (e.g. hardness, strength, ductility).

Further, with respect to modeling and simulation, $P_{net}$ is a critical variable that can help in the prediction of thermal conditions; melt pool characteristics, bead geometry, integrity, and properties; distortion. The ability to directly measure $P_{net}$ is therefore necessary to validate models to improve the understanding of molten metal manufacturing processes like additive manufacturing. Despite the need to measure and know net power prior designs aimed at monitoring metal additive manufacturing typically resort to the indirect technique of measuring melt pool size then correlating back to the more complex thermal characteristics. As discussed above, while such an approach is a practical approach, it offers little insight for model refinement compared to the parsing of the energy during a build.

Giving full appreciation to the above, the Applicants have discovered the critical importance of measuring $P_{net}$, and devised a system to for obtaining the same. While the invention herein will be described in the context of additive manufacturing, it also has application in any solidification manufacturing process where it is desirable to monitor energy input into a system.

In one aspect, the invention provides a calorimeter head. An embodiment of such a calorimeter head includes a base unit. The base unit includes a body and a removable substrate plate attached to the body. The substrate plate and body define a cavity. The body includes a plurality of inlet ports. The plurality of inlet ports are equally spaced and tangentially arranged relative to a maximum diameter of the cavity. The body also includes a main outlet port in fluid communication with the cavity. The calorimeter head also includes an inlet manifold attached to the base unit. The inlet manifold has a main inlet port and a plurality of manifold outlet ports. A flow path extends from the main inlet port through the plurality of manifold outlet ports to the plurality of inlet ports of the body. This flow path then extends from the plurality of inlet ports through the cavity to the main outlet port.

In an embodiment according to this aspect, the cavity is defined by a bottom surface of the substrate plate, a cylindrical sidewall formed in the body, and a conical bottom wall extending from the cylindrical sidewall and formed in the body. The plurality of inlet ports are formed in the cylindrical sidewall of the cavity. The conical bottom wall is truncated and terminates with a drain port. The drain port is in fluid communication with the main outlet port. The plurality of inlet ports have a combined first cross sectional area, and the drain port has second cross sectional area. The combined first cross sectional area is not more than ten percent larger than the second cross sectional area.

In an embodiment according to this aspect, the cavity has a maximum height which is less than or equal to half of the maximum diameter of the cavity.

In an embodiment according to this aspect, the plurality of inlet ports includes three inlet ports which are arranged at an angle of 120° relative to one another. The plurality of manifold outlet ports includes three manifold outlet ports arranged at an angle of 120° relative to one another. The main inlet port is arranged along an axis normal to a plane through which the three manifold outlet ports extend.

In an embodiment according to this aspect, the calorimeter head also includes a clamping arrangement for clamping the substrate plate against the body. The clamping arrangement includes a clamping ring, an adapter ring, and a plurality of clamps. The plurality of clamps clamp the clamping ring against the adapter ring such that the adapter ring and clamping ring exert an axial force against the substrate plate, thereby biasing the substrate plate against the body. A seal may also be positioned between the substrate and body.

In another aspect, the invention provides a calorimeter head. An embodiment of a calorimeter head according to this aspect includes a base unit. The base unit comprises a body and a removable substrate plate attached to the body. The substrate plate and body define a cavity. The cavity is defined by a bottom surface of the substrate plate, a cylindrical sidewall and a conical bottom wall extending from the cylindrical sidewall. The conical bottom wall terminates at a drain port. The body includes a plurality of inlet ports. An inlet manifold is attached to the base unit. The inlet manifold has a main inlet port and a plurality of manifold outlet ports. The plurality of manifold outlet ports are in fluid communication with the plurality of inlet ports.

In an embodiment according to this aspect, the cavity has a maximum diameter. The plurality of inlet ports are equally spaced and tangentially arranged relative to the maximum diameter. The plurality of inlet ports includes three inlet ports arranged at an angle of 120° relative to one another. The plurality of manifold outlet ports includes three manifold outlet ports arranged at an angle of 120° relative to one another.

In an embodiment according to this aspect, the cavity has a maximum height extending between the drain port and an uppermost edge of the cylindrical side. The height is less than or equal to half of the maximum diameter of the cavity.

In yet another aspect, the invention provides a calorimeter system. An embodiment of such a calorimeter system includes a control unit. A calorimeter head is fluidly and electrically coupled to the control unit. A coolant flow loop extends from the control unit to the calorimeter head and back to the control unit. The calorimeter head includes a plurality of inlet ports equally spaced and tangentially arranged relative to a cavity of the calorimeter head. The plurality of inlet ports are arranged to receive a coolant flow via the coolant flow loop from the control unit. The calorimeter head includes a drain port in fluid communication with the plurality of inlet ports via a cavity of the calorimeter head. The calorimeter head includes a main outlet port arranged to return the coolant flow to the control unit via the coolant flow loop.

In an embodiment according to this aspect, the control unit includes a controller, a coolant supply unit, and a chiller. The coolant supply unit configured to convey coolant through the coolant flow loop. The coolant supply unit is connected to a main inlet port of the calorimeter head via an inlet conduit, and wherein the chiller is connected to a main outlet port of the calorimeter head. The plurality of inlet ports have a combined first cross sectional area, wherein the drain port has second cross sectional area, wherein the combined first cross sectional area is larger than the second cross sectional area. In a subsidiary embodiment, the combined first cross sectional area is not more than ten percent larger than the second cross sectional area.

In an embodiment according to this aspect, the coolant supply unit includes a thermally insulated accumulator. The control unit may also include a precision resistor circuit for thermal calibration. The precision resistor circuit is integrated with the coolant supply unit. The precision resistor circuit may also be part of a separate calibration unit.

Other aspects, objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

Turning now to the drawings, embodiments of a calorimeter head and an associated system according to the teachings of the present invention are shown and described. As will be understood from the following, the invention provides a highly accurate and precise thermal sensing device and system which allows for the determination of the net power introduced by a directed energy heat source during solidification manufacturing processes (e.g. a laser or electron beam in an additive manufacturing process). With this device and system, tighter control over solidification manufacturing processes may be achieved, and in particular, build geometries and build material properties may be reliably produced. While the embodiments described herein will be discussed in the context of additive manufacturing, the calorimeter device and system may be readily applied in other applications where the use of a calorimeter is desirable for directed energy input measurement in a manufacturing build cell. Other exemplary applications include but are not limited to laser, electron beam, and arc welding processes.

Figure 1:
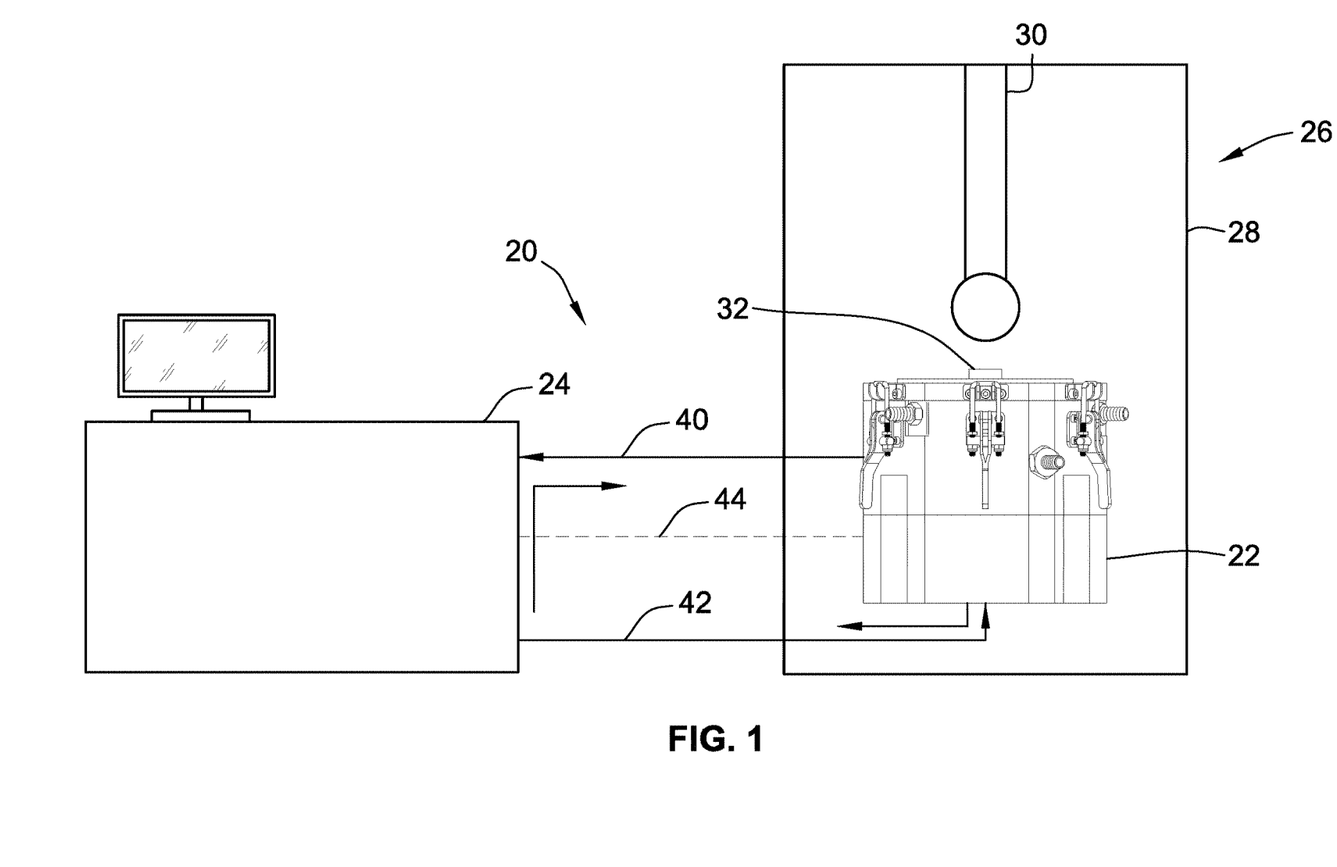
FIG. 1 is a schematic view of an exemplary embodiment of a uniform chilling calorimeter system according to the teachings herein associated with a schematically represented additive manufacturing machine.

Turning now to FIG. 1, an exemplary embodiment of a calorimeter system 20 is illustrated. Calorimeter system 20 includes a calorimeter head 22 and a control unit 24. Calorimeter system 20 is employed in the context of an additive manufacturing system 26. This additive manufacturing system 26 includes in schematic form a housing 28 with a directed energy heat source 30 therein. Typically, this heat source 30 is a laser for fusing a powdered metal into a solid form during the additive manufacturing process. As illustrated schematically, a work piece 32 is positioned under the directed energy heat source 30. This work piece 32 may be positioned or formed directly on calorimeter head 22. Calorimeter head 22 is operable to detect the energy input from heat source 30 into work piece 32.

This determination allows for the highly accurate and precise control of the additive manufacturing process. Such control may be achieved via a direct feedback loop wherein the readings collected by calorimeter system 20 are delivered directly to the control system of the additive manufacturing system 26 for real-time adjustments of solidification manufacturing process parameters. Alternatively, calorimeter system 20 may be employed as a calibration device useful for initially calibrating an additive manufacturing system 26. Still further, calorimeter system 20 may be employed as a means for monitoring the quality of incoming feedstock thermal characteristics in order to compensate for small perturbations.

As schematically illustrated, an inlet conduit 40 extends from control unit 24 to calorimeter head 22. This inlet conduit is operable to deliver a coolant flow of coolant to calorimeter head 22. An outlet conduit 42 extends from calorimeter head 22 back to control unit 24. As such, a coolant flow loop exists between control unit 24 and calorimeter head 22 by way of inlet and outlet conduits 40, 42. Coolant is circulated through this coolant flow loop. Data is collected relative to the energy transferred to the coolant after it is circulated through calorimeter head 22. This data is then used ultimately for a determination of the energy input provided by directed energy heat source 30 to work piece 32. "Coolant" as used herein means any heat transfer medium. As one non-limiting example, the coolant may be water. As another non-limiting example, the coolant may be a liquid sodium.

Additionally, an electrical connection 44 extends between control unit 24 and calorimeter head 22. This electrical connection delivers electrical signals collected by temperature sensors of calorimeter head 22. As discussed below, these temperature sensors may be thermopiles, thermistors, thermocouples, RTD sensors, or any other sensor useful for detecting the temperature of flowing coolant. Although illustrated as a single line of connection, electrical connection 44 may comprise multiple connection lines, e.g. multiple connections for multiple sensors.

Figure 2:
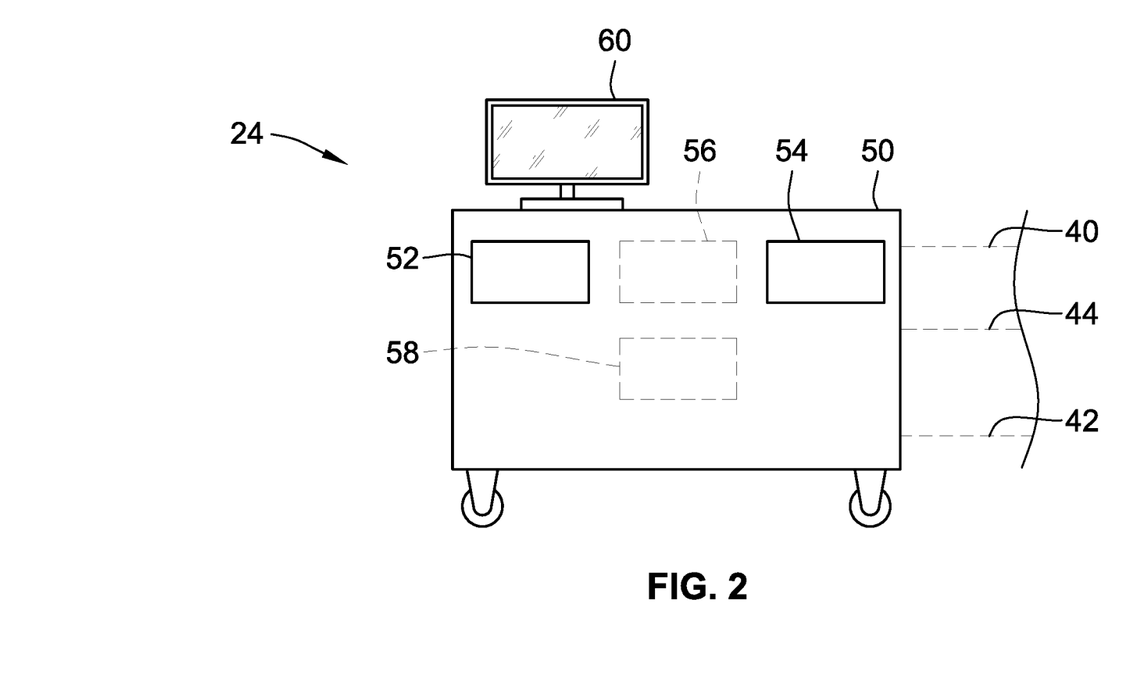
FIG. 2 is a schematic view of a control unit of the system of FIG. 1.

Turning now to FIG. 2, a description of control unit 24 will be provided. Control unit 24 includes an outer housing 50 within which a controller 52 and coolant supply unit 54 are situated. Controller 52 is operable to control the operation of coolant supply unit 54. Coolant supply unit 54 may include a pump, thermal stabilizing accumulator, control valves for flow control in normal run operation, and an internal calibration circuit for initial calibration during a calibration mode, or any combination of such componentry used to deliver a steady and controlled mass flow of coolant via the above-introduced coolant flow loop at a desired pressure. The aforementioned internal calibration circuit may include a precision resistor circuit such as a 1% resistor used to internally calibrate the thermal measurement. This calibration circuit may also be provided via separate calibration unit 58 discussed below. Further, coolant supply unit may include or utilize solenoid actuated valves and/or flow meters for monitoring flow rate and controlling fluid flow, as well as a variable valve that allows for control of a constant mass flow rate of coolant through the coolant flow loop.

Control unit 24 also includes a chiller 56 useful for maintaining the coolant flowing from control unit 24 at a constant chilled temperature. In an exemplary configuration, coolant is chilled by chiller 56 to a constant temperature (approximately +/−0.1° C. of a desired starting temperature) and delivered to coolant supply unit 54. Chiller 56 thus may take the form of any contemporary chiller device operable to achieve and maintain the above constant temperature. The operation of chiller is controlled via controller 52, which includes all of the necessary firmware, software, and hardware necessary to achieve the functionality thereof described herein. It is also envisioned that coolant may first be chilled by chiller 56 which is external to control unit 24, and then flow through control unit 54 as described herein.

This coolant is then provided by coolant supply unit 54 to inlet conduit 40 and then flows through calorimeter system 20 and a temperature change therein is detected by the aforementioned sensors. Heat is transferred to the coolant from calorimeter head 22 as described below, thereby causing an increase in temperature of the coolant. The coolant then returns via outlet conduit 42 to chiller 56. Controller 52 is operable to collect and interpret data delivered via electrical connection 44 as well as collected internally by control unit 24 with regard to the coolant flow through the coolant flow loop. A user interface 60 may be provided for presentation of the data collected by controller 52, as well as providing a means for providing input control commands to calorimeter system 20.

Although illustrated as incorporating coolant supply unit 54 and chiller 56 internally within housing 50, it is contemplated that these components may be external to housing 50. Still further, control unit 24 may also include a stand-alone calibration unit 58 for providing an initial calibration of calorimeter system 20. Such a calibration unit 58 may operate by introducing a known temperature increase to the coolant flow through the aforementioned coolant flow loop which in turn is set at either or both of calorimeter head 22 and control unit 24. As previously stated, this calibration unit 58 may include the above described precision resistor circuit. Although shown internally within housing 50, calibration unit 58 may also be situated external to housing 50. Additionally, it will be recognized that appropriate conduit, valving, etc. is utilized to connect the various components of control unit 24 to each other to achieve the functionality described above.

Figure 3:
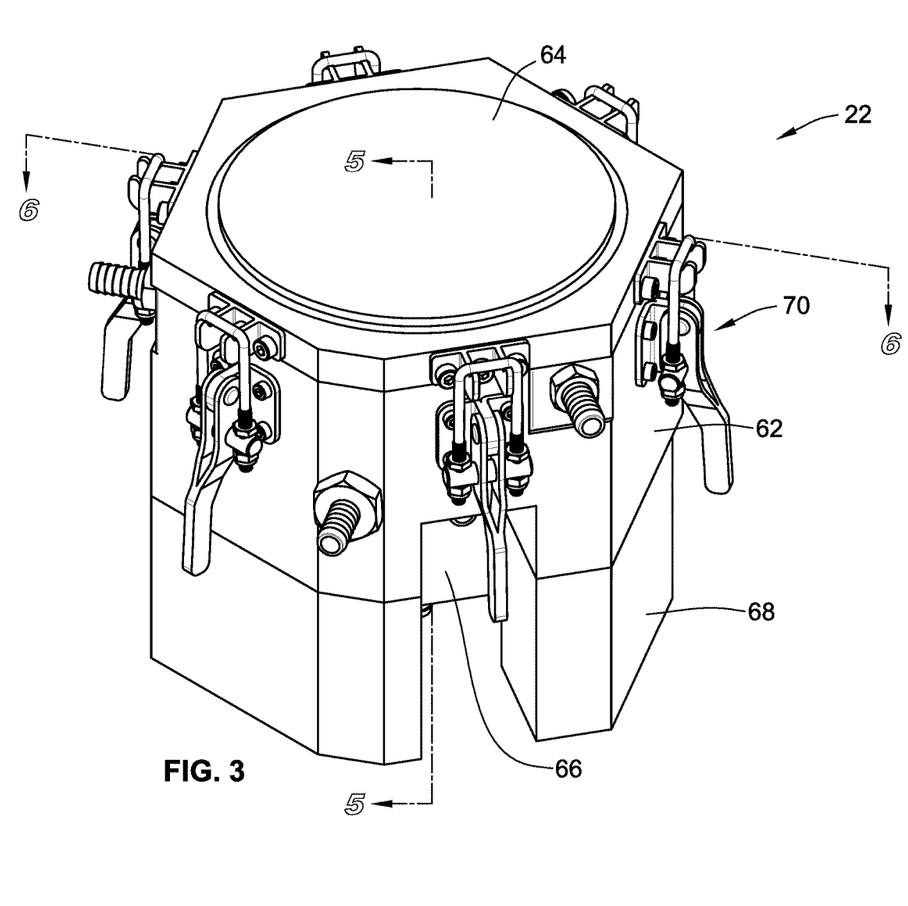
FIG. 3 is a perspective view of a calorimeter head of the system of FIG. 1.

Turning now to FIG. 3, the particulars of calorimeter head 22 will be discussed. Calorimeter head 22 includes a base unit 62 with a build plate in the form of a removable substrate plate 64 attached to the base unit 62. Although illustrated as a having a flat upper surface, this upper surface on substrate plate 64 may take on other geometries to accommodate the particular build process. A hydraulic inlet manifold 66 is attached to base unit 62 and is operable to distribute the coolant flow from the coolant flow loop to base unit 62 as described below. Base unit 62 may employ a number of legs 68 to provide clearance for inlet manifold 66 which is positioned generally beneath base unit 62. These legs 68 may be integral to base unit 62 or may be removed separately. Calorimeter head 22 also includes a clamping arrangement 70 for sealing the removable substrate plate 64 to base unit 62 as discussed below.

Figure 4:
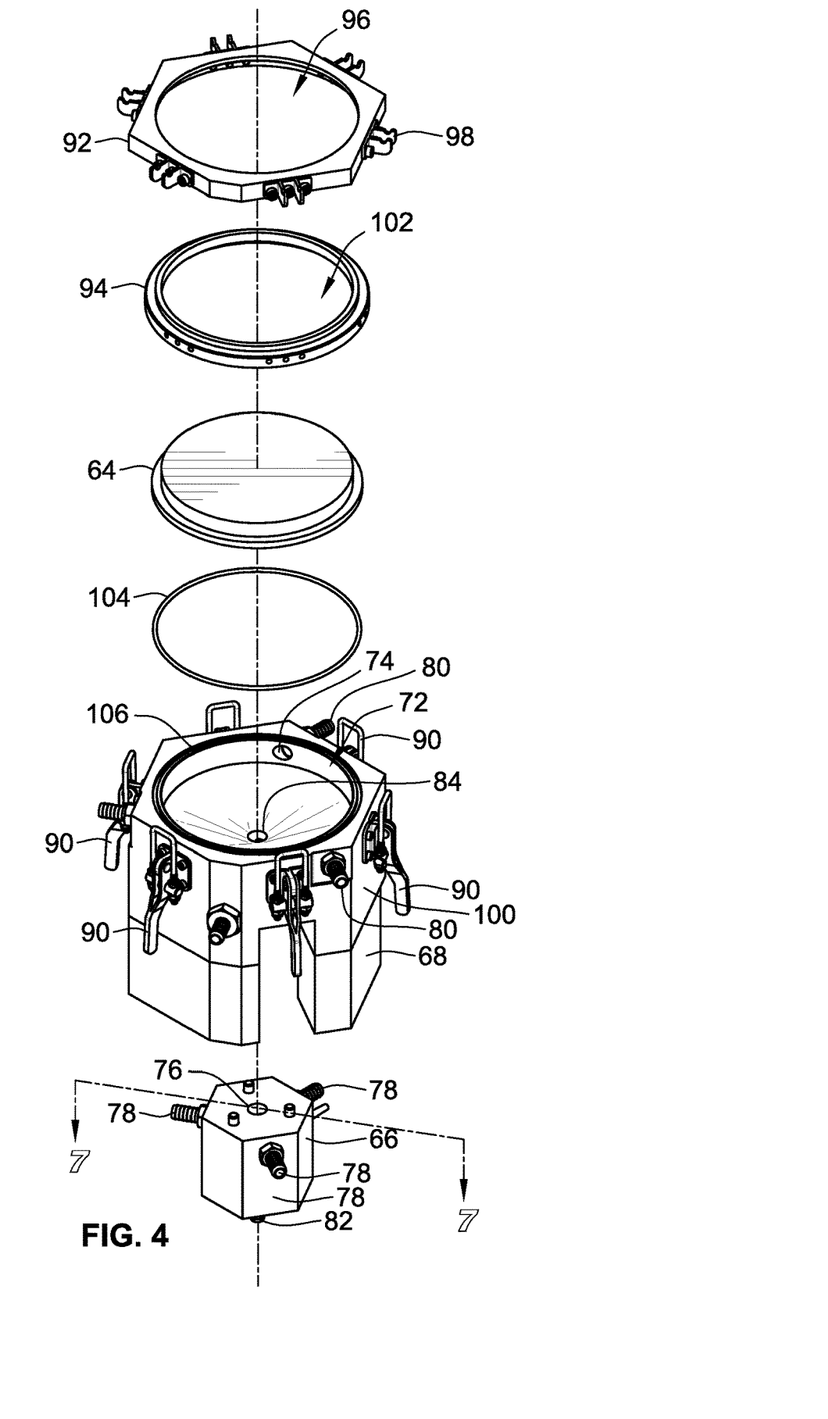
FIG. 4 is an exploded perspective view of the calorimeter head of FIG. 3.

Turning now to FIG. 4, calorimeter head 22 is illustrated in an exploded view. As can be seen in this view, a cavity 72 is defined (i.e. bounded) by a body 100 of base unit 62 and a bottom surface of substrate plate 64. Cavity 72 receives the coolant flow via a plurality of inlet ports 74 tangentially arranged relative to a maximum diameter $D_1$ of cavity 72, as described below. These inlet ports 74 receive coolant by way of inlet manifold 66. More particularly, coolant enters inlet manifold 66 via a main inlet port 114 (See FIG. 5). This coolant is then distributed through inlet manifold 66 and exits the same via a plurality of manifold outlet ports 112 (See FIG. 5). Coolant exiting these manifold outlet ports 112 is delivered to the aforementioned inlet ports 74. Although not illustrated, it will be readily appreciated that flexible conduit is used to interconnect manifold outlet ports 112 to inlet ports 74. In steady-state operation, air is evacuated from cavity 72 such that only flowing coolant is present therein. Given the tangential arrangement of inlet ports 74, a continuous vortex of coolant exists within cavity 72 which directly shears along the bottom surface of substrate plate 64.

Figure 7:
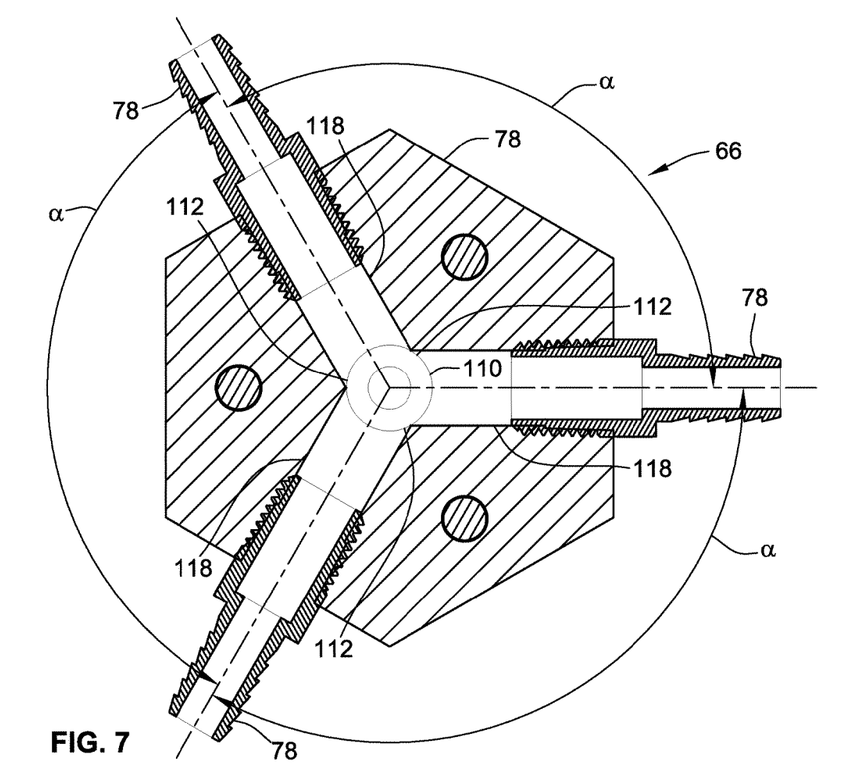
FIG. 7 is another cross section of the inlet manifold of FIG. 7, showing a plane normal to the plane shown in FIG. 5.

As can be seen in FIGS. 4 and 7, there are three equally spaced manifold outlet ports 112 (See FIG. 7) and three equally spaced inlet ports 74 (See FIG. 4). Each outlet port 112 is connected to each inlet port 74 in a one-to-one relationship. Such connection may be achieved by way of flexible tubing or the like. Further, a connector 78 is associated with each one of the plurality of manifold outlet ports 112. Similarly, a connector 80 is associated with each of the plurality of inlet ports 74. Additionally, a connector 82 is also associated with main inlet port 114. These connectors 78, 80, 82 are illustrated as hose barb connectors, although any other type of connector may be utilized.

Still referring to FIG. 4, as mentioned above, a removable substrate plate 64 attached to body 100 by way of a clamping arrangement 70 (See also FIG. 3). This clamping arrangement 70 includes a plurality of clamps 90 fixed to body 100. Clamping arrangement 70 also includes a clamping ring 92 which defines a central opening 96 therein. Clamping arrangement 70 also includes an adapter ring 94 defining its own central opening 102 positioned below clamping ring 92 as illustrated. Clamps 90 connect to clamp receivers 98 and bias clamping ring 92 and adapter ring 94 against a flange of substrate plate 64 to axially bias substrate plate 64 against body 100. As can be seen in FIG. 3, a portion of substrate pate 64 protrudes through openings 96, 102. Additionally, a seal 104 is provided between substrate plate 64 and body 100 to ensure there is no leakage between this interface between substrate plate 64 and body 100. This seal 104 may be received in a seal groove 106 formed in body 100 as shown.

Figure 5:
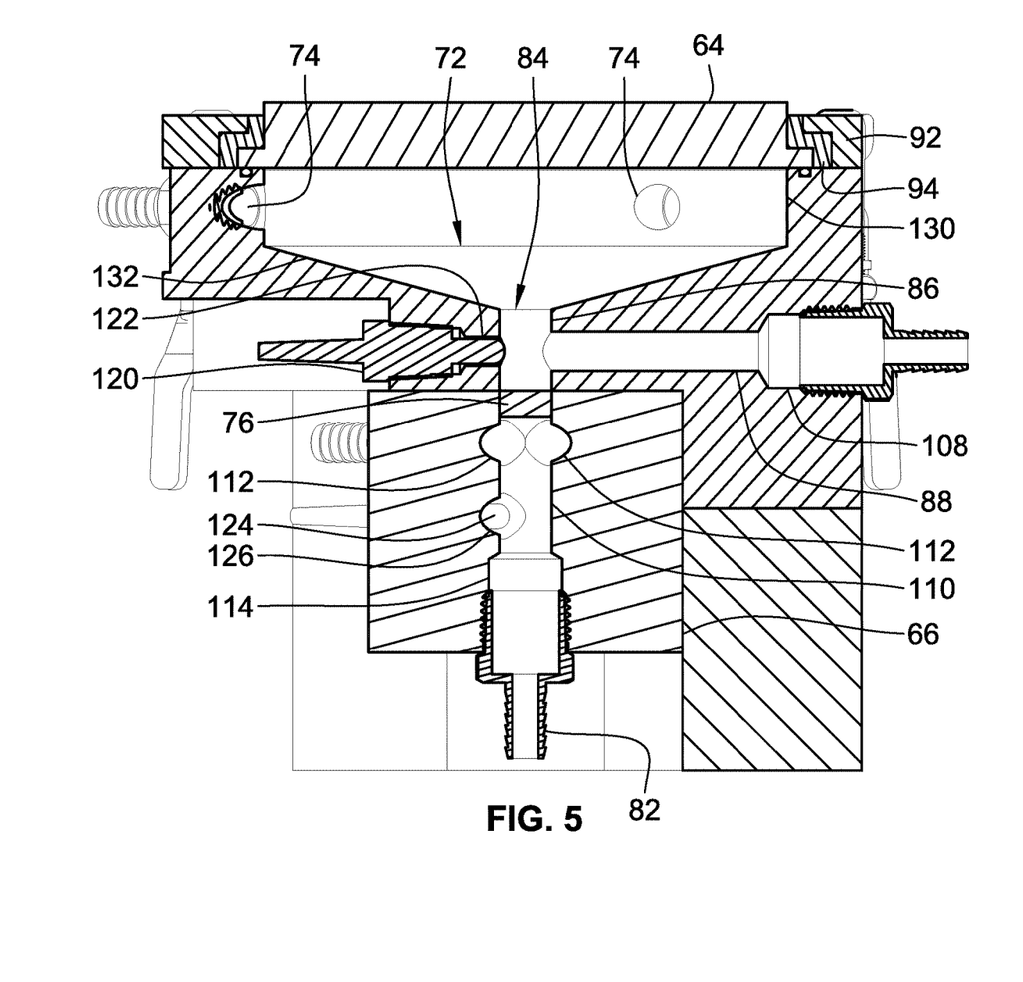
FIG. 5 is cross section of the calorimeter head of FIG. 3, showing a plane passing through an intermediary outlet of the calorimeter head.

Turning now to FIG. 5, calorimeter head 22 is shown in cross-section to expose the particular geometry of the aforementioned cavity 72. As discussed above, cavity 72 is defined by a bottom surface of substrate plate 64, a cylindrical sidewall 130 formed in body 100, and a conical bottom wall 132 depending from cylindrical sidewall 130 and terminating at a drain port 84. The cylindrical sidewall 130 defines a maximum diameter of cavity 72. Cavity 72 also has a height which extends from the uppermost edge of cylindrical sidewall 130 to drain port 84. This height is less than or equal to half of the afore-mentioned maximum diameter.

Drain port 84 connects to a drain conduit 86 which in turn connects to a main drain outlet conduit 88. Main drain outlet conduit 88 terminates at a main outlet port 108. Coolant entering cavity 72 through inlet ports 74 passes through drain port 84, conduits 86, 88 and exits calorimeter head 22 at main outlet port 108. This coolant is then returned via the afore-mentioned coolant flow loop to control unit 24. In particular, flexible tubing or conduit connects to connector 80 attached at main outlet port 108. This tubing or conduit defines the afore-mentioned outlet conduit 42 shown in FIG. 1.

The total cross sectional area of the inlet ports 74 is closely sized to that of the cross sectional area of drain port 84. This sizing reduces or eliminates unwanted turbulence and balances the combined inlet flow rate with the outlet flow rate. Such a configuration aids in solidification manufacturing process sensitivity. Further, such a configuration aids in the removal air trapped in cavity 72 at startup. Accordingly, while it is contemplated that calorimeter system 20 utilizes a closed flow system, the same include air ventilation capabilities to vent air removed from cavity 72.

It has been found that air bubbles trapped in cavity 72 can lead to large thermal gradients on the surface of substrate plate 64.

As one non-limiting example of port area sizing, the combined cross sectional area of the inlet ports 74 may be 0.450 in$^2$, while the cross sectional area of the drain may be 0.40 in$^2$. The foregoing results in a difference of less than ten percent in the combined cross sectional area of inlet ports 74 and the cross sectional area of drain port 84. Cross sectional area in the foregoing is taken to mean that area which is normal to the direction of fluid flow through the port. It has been found that maintaining this difference of less than ten percent, optimal performance is achieved. It is also contemplated that the combined cross sectional area of inlet ports 74 may be equal to the cross sectional area of drain port 84. With the above area matching, it has been found that a thermal gradient across a 5.5 inch diameter substrate plate 64 is less than one degree Celsius.

Still referring to FIG. 5, a temperature sensor 120 is positioned within a passageway 122 in communication with drain conduit 86. This temperature sensor 120 is operable to collect the temperature of the coolant exiting cavity 72. Temperature sensor 120 may take on any known form of a temperature sensor, and as non-limiting examples, may be a thermopile, thermo-couple, thermistor, or RTD-type sensor.

Another temperature sensor is positioned in inlet manifold 66. This temperature sensor 124 is positioned within a passageway 126 which is in communication with a main inlet passageway 110 of inlet manifold 66. As can be seen in FIG. 5, this main inlet passageway 110 is in communication with main inlet port 114, which as discussed above, connects to inlet conduit 40 shown in FIG. 1. Temperature sensor 124 is situated such that it may detect a temperature of the coolant entering inlet flow manifold 66. This temperature reading is taken just prior to the coolant entering the plurality of manifold outlet ports 112 of inlet manifold 66.

As can be seen in FIG. 5, the plurality of manifold outlet ports 112 are in communication with main inlet port 114 via main inlet passageway 110. These ports 112 are arranged to evenly distribute coolant entering inlet manifold 66 to the plurality of inlet ports 74 for symmetric entry in cavity 72. As can also be seen in FIG. 5, a plug or cap 76 is situated within main inlet passageway 110 to close the same such that coolant entering inlet manifold 66 must exit the same via manifold outlet ports 112. This cap or plug 76 also prevents coolant from cavity 72 from cross-contaminating the coolant flowing through inlet manifold 66.

Figure 6:
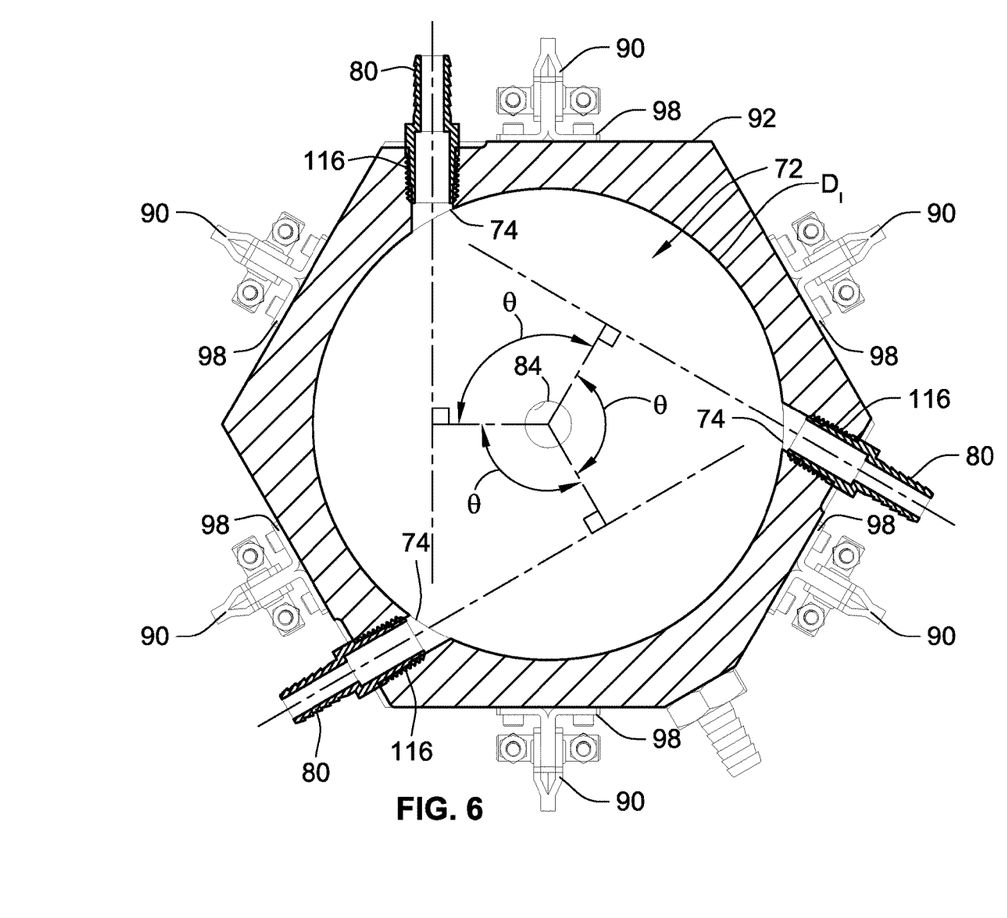
FIG. 6 is a another cross section of the calorimeter head of FIG. 3, showing a plane normal to the plane shown in FIG. 5.

Turning now to FIG. 6, the same illustrates a cross-section taken through the plane passing through the plurality of inlet port 74. As can be seen in this view, each of the plurality of inlet ports 74 are spaced an angle of θ relative to one another. In the instant arrangement, three ports are provided which are equally spaced at an angle θ of 120°. As can also be seen in this view, the ports are arranged such they are tangential to a diameter $D_1$ of cavity 72.

As can be surmised from FIG. 6, by tangentially arranged it is meant that the central axes extending through the ports shown do not coincide with the center of cavity 72, i.e. the center of diameter $D_1$. This tangential arrangement provides for a highly stable vortex flow within cavity 72 shear the bottom surface of the substrate to promote the desirable uniform heat transfer from substrate 64 to the coolant circulating therein. Each inlet port 74 connects to an inlet passageway 116 as shown which is formed through body 100. As introduced above, connectors 80 are situated within passageways 116 for connection of conduit to fluidly communicate inlets 74 with outlets 112 (See FIG. 5).

Turning now to FIG. 7, another cross-section is taken through the plane extending through the plurality of outlets 112 of inlet manifold 66. As can be seen in this view, the plurality of manifold outlet ports 112 are arranged in a similar fashion to the plurality of inlet port 74 shown in FIG. 6. More specifically, these ports 112 are equally spaced from one another at an angle α. As shown in FIG. 7, there are three ports 112 which are spaced at an angle α of 120°. As may also be surmised from this view, these ports 112 connect to passageways 118 through inlet manifold 66. Connectors 80 are situated within passageways 118 and facilitate fluid communications between ports 112 and ports 74 as described above. Also as can be surmised from this view, these ports 112 are not tangentially arranged relative to the diameter $D_1$ of cavity 72. Indeed, the center line extending through each port 112 intersects or coincides with the center of the aforementioned diameter $D_1$.

In a further embodiment, it is contemplated that the base unit 62, inlet manifold 66, and/or clamping arrangement may be manufactured from a thermally insulating material to prevent heat loss of coolant flowing through the system to the outside environment. As a non-limiting example any of the components mentioned above, as well as their constituent subcomponents, may be formed of a nylon material or any other material recognized as providing good thermal insulation properties.

With the foregoing structural description in hand, a brief description of a typical operation of calorimeter system 20 will be provided with reference to the embodiment shown in the figures. First, coolant is supplied via inlet conduit 40 to calorimeter head 22 via coolant supply unit 54. This coolant is chilled via chiller 56 to a controlled, steady state temperature. The supply of coolant from coolant supply unit 54 is such that a constant mass flow rate is achieved. The coolant then enters main inlet port 114 of manifold 66. This coolant then passes by temperature sensor 126 mounted to manifold 66 and a temperature reading is taken. The coolant then exits via the plurality of manifold outlet ports 112 of manifold 66.

Coolant leaving manifold outlet ports 66 then passes through the plurality of inlet ports 74 and enters cavity 72. Heat is transferred from substrate plate 64 to the coolant flowing in cavity 72. The coolant then exits drain port 84 communicating with cavity 72. This coolant then passes by temperature sensor 124 and another temperature reading is taken. As such, a temperature reading before and after the above described heat transfer occurs. The coolant then exits a main outlet port 108 and returns to chiller via an outlet conduit 42.

Because the mass flow rate and temperature before and after heat transfer are known, and because the system also takes into account other known parameters such as the power of the directed energy heat source (e.g. the laser), travel speed of the power source, build layer thickness and hatch distance, build volume, and beam diameter, various parameters may be calculated such as $P_{net}$, total theoretical and measured energy, theoretical and measured energy density, laser transfer efficiency, net heat input, global energy density.

As will be understood from the foregoing, calorimeter system 20 advantageously provides a means for determining the energy input into a workpiece during a manufacturing process. Calorimeter system 20 may be employed as a system for providing real-time solidification manufacturing process monitoring, as well as for calibration of a directed energy source of a solidification manufacturing process such as additive manufacturing, as well as for quality control of feedstock utilized in such processes.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A calorimeter head, comprising:
   a base unit, the base unit comprising a body, and a removable substrate plate removably attached to the body, the substrate plate and body defining a cavity, the body including a plurality of inlet ports, the plurality of inlet ports equally spaced and tangentially arranged relative to a maximum diameter of the cavity, the body also including a main outlet port in fluid communication with the cavity;
   an inlet manifold attached to the base unit, the inlet manifold having a main inlet port and a plurality of manifold outlet ports; and
   wherein a flow path extends from the main inlet port through the plurality of manifold outlet ports to the plurality of inlet ports of the body, and from the plurality of inlet ports through the cavity to the main outlet port.

2. The calorimeter head of claim 1, wherein the cavity has a maximum height which is less than or equal to half of the maximum diameter of the cavity.

3. The calorimeter head of claim 1, further comprising a clamping arrangement for clamping the substrate plate against the body, wherein the clamping arrangement includes a clamping ring, a adapter ring and a plurality of clamps, the plurality of clamps clamping the clamping ring against the adapter ring such that the adapter ring and clamping ring exert an axial force against the substrate plate, biasing the substrate plate against the body.

4. The calorimeter head of claim 3, further comprising a seal positioned between the substrate plate and body.

5. The calorimeter head of claim 1, wherein the plurality of inlet ports includes three inlet ports arranged at an angle of 120° relative to one another.

6. The calorimeter head of claim 5, wherein the plurality of manifold outlet ports includes three manifold outlet ports arranged at an angle of 120° relative to one another.

7. The calorimeter head of claim 6, wherein the main inlet port is arranged along an axis normal to a plane through which the three manifold outlet ports extend.

8. The calorimeter head of claim 1, wherein the cavity is defined by a bottom surface of the substrate plate, a cylindrical sidewall formed in the body, and a conical bottom wall extending from the cylindrical sidewall and formed in the body.

9. The calorimeter head of claim 8, wherein the plurality of inlet ports are formed in the cylindrical sidewall of the cavity.

10. The calorimeter head of claim 8, wherein the conical bottom wall is truncated and terminates with a drain port, the drain port in fluid communication with the main outlet port, wherein the plurality of inlet ports have a combined first cross sectional area, wherein the drain port has second cross sectional area, wherein the combined first cross sectional area is not more than ten percent larger than the second cross sectional area.

11. A calorimeter head, comprising:
    a base unit, the base unit comprising a body and a removable substrate plate attached to the body, the substrate plate and body defining a cavity, the cavity defined by a bottom surface of the substrate plate, a cylindrical sidewall and a conical bottom wall extending from the cylindrical sidewall, the conical bottom wall terminating at a drain port and wherein the body includes a plurality of inlet ports; and
    an inlet manifold attached to the base unit, the inlet manifold having a main inlet port and a plurality of manifold outlet ports, the plurality of manifold outlet ports in fluid communication with the plurality of inlet ports.

12. The calorimeter head of claim 11, wherein the cavity has a maximum diameter, and wherein the plurality of inlet ports are equally spaced and tangentially arranged relative to the maximum diameter.

13. The calorimeter head of claim 12, wherein the cavity has a maximum height extending between the drain port and an upper-most edge of the cylindrical sidewall, wherein the height is less than or equal to half of the maximum diameter.

14. The calorimeter head of claim 12, wherein the plurality of inlet ports includes three inlet ports arranged at an angle of 120° relative to one another.

15. The calorimeter head of claim 14, wherein the plurality of manifold outlet ports includes three manifold outlet ports arranged at an angle of 120° relative to one another.

16. A calorimeter system, the calorimeter system comprising:

a control unit;

a calorimeter head fluidly and electrically coupled to the control unit, wherein a coolant flow loop extends from the control unit to the calorimeter head and back to the control unit;

wherein the calorimeter head includes a plurality of inlet ports equally spaced and tangentially arranged relative to a cavity of the calorimeter head, the plurality of inlet ports are arranged to receive a coolant flow via the coolant flow loop from the control unit, and wherein the calorimeter head includes a drain port in fluid communication with the plurality of inlet ports via a cavity of the calorimeter head; and wherein the calorimeter head includes a main outlet port returning the coolant flow to the control unit via the coolant flow loop.

17. The calorimeter system of claim 16, wherein the plurality of inlet ports have a combined first cross sectional area, wherein the drain port has second cross sectional area, wherein the combined first cross sectional area is larger than the second cross sectional area.

18. The calorimeter system of claim 17, wherein the combined first cross sectional area is not more than ten percent larger than the second cross sectional area.

19. The calorimeter system, of claim 16, wherein the control unit includes a controller, a coolant supply unit, and a chiller, the coolant supply unit configured to convey coolant through the coolant flow loop.

20. The calorimeter system of claim 19, wherein the coolant supply unit is connected to a main inlet port of the calorimeter head via an inlet conduit, and wherein the chiller is connected to a main outlet port of the calorimeter head.

21. The calorimeter system of claim 19, wherein the coolant supply unit includes a thermally insulated accumulator.

22. The calorimeter system of claim 19, wherein the control unit further comprises a precision resistor circuit for thermal calibration.

23. The calorimeter system of claim 22, wherein the precision resistor circuit is integrated with the coolant supply unit.

24. The calorimeter system of claim 22, wherein the precision resistor circuit is part of a separate calibration unit.

* * * * *